United States Patent

Esch et al.

[11] Patent Number: 5,883,261
[45] Date of Patent: Mar. 16, 1999

[54] PROCESS FOR THE MANUFACTURE OF ALKYLIMIDAZOLIDONE (METH)-ACRYLATES

[75] Inventors: Marc Esch, Merlebach; Alain Riondel, Forbach, both of France

[73] Assignee: Elf Atochem S.A., France

[21] Appl. No.: 931,284

[22] Filed: Sep. 16, 1997

[30] Foreign Application Priority Data

Sep. 16, 1996 [FR] France .................................. 96 11270

[51] Int. Cl.$^6$ .............................................. C07D 233/14
[52] U.S. Cl. ...................................................... 548/324.1
[58] Field of Search ........................................... 548/324.1

[56] References Cited

U.S. PATENT DOCUMENTS 2,871,223  11/1959  Hankins et al. .......................... 260/70

FOREIGN PATENT DOCUMENTS 0 236 994   9/1987   European Pat. Off. .
0 571 851  12/1993   European Pat. Off. .
0 650 962   5/1995   European Pat. Off. .

*Primary Examiner*—Joseph K. McKane
*Attorney, Agent, or Firm*—Millen, White, Zelano, & Branigan, P.C.

[57] ABSTRACT

Process for the manufacture of a compound of formula (I) by reaction of at least one (meth)acrylate of formula (II) with a heterocyclic alcohol of formula (III) in the presence of sodium methoxide as catalyst, characterized in that the sodium methoxide is gradually introduced, as a solution, throughout the synthesis:

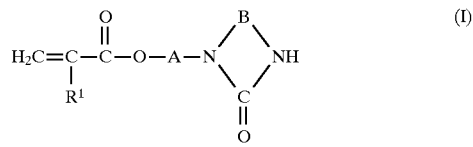

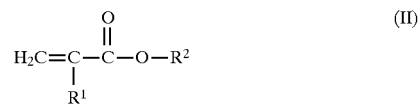

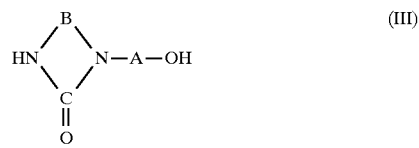

$R^1$=hydrogen or methyl; A and B each independently represent a straight or branched hydrocarbon chain having from 2 to 5 carbon atoms; $R^2=C_1-C_4$ alkyl group.

19 Claims, No Drawings

PROCESS FOR THE MANUFACTURE OF ALKYLIMIDAZOLIDONE (METH)-ACRYLATES

BACKGROUND OF THE INVENTION

The present invention relates to a process for the manufacture of a compound of formula:

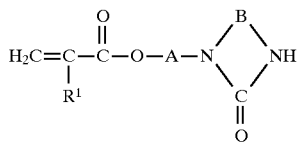

in which:

$R^1$ represents hydrogen or methyl;

A and B each independently represent a straight or branched hydrocarbon chain having from 2 to 5 carbon atoms, by reaction of at least one (meth)acrylate of formula:

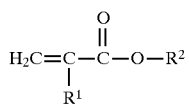

in which:

$R^1$ has the abovementioned meaning; and $R^2$ represents a $C_1$-$C_4$ alkyl group, with a heterocyclic alcohol of formula:

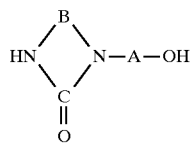

in which A and B have the abovementioned meanings.

These compounds of formula (I) are known for their role in the formation of polymers useful as coatings and adhesives, for the treatment of paper and textiles, in particular by U.S. Pat. No. 2,871,223, as well as for their uses as leather treatment agents, and in the production of emulsion paints. Ethylimidazolidone methacrylate (EIOM) is mainly used in paints as a wet-adhesion promoter.

The synthesis of EIOM by transesterification has already formed the subject of a great many patents, which differ from one another in the nature of the catalyst used. Solid or partly solid catalysts, which make it possible to operate at a temperature below 100° C. while giving good results from the viewpoint of the EIOM yield and of the conversion of EIOH (1-(2-hydroxyethyl)imidazolidyl-2-one [sic]), have been discovered. It appears, however, that it might be possible to make the synthesis even easier to operate on an industrial scale if a liquid catalyst offering the same advantages were to be provided for this reaction.

SUMMARY OF THE INVENTION

European Patent Application EP-A-0,236,994 reports the use of sodium methoxide as catalyst of this reaction but with the recommendation of not using it because of its strong propensity to promote side reactions (Michael addition, in particular). However, it has now been discovered, surprisingly, that this catalyst can be used very advantageously, giving good results with respect to the EIOM yield and with respect to the conversion of EIOH, without resulting in the predicted disadvantage of promoting side reactions, provided that it is introduced not in a single step (usual conditions of use) at the beginning of the synthesis but distributed throughout the synthesis.

The subject of the present invention is thus the process for the manufacture of a compound of formula (I), as it has been defined above, in the presence of sodium methoxide as catalyst, this process being characterized in that the sodium methoxide is gradually introduced, as a solution, throughout the synthesis.

In accordance with a particularly preferred embodiment of the process according to the invention, a portion of the sodium methoxide is introduced at the beginning of the synthesis and the remainder is introduced, continuously or in fractions, throughout the synthesis. The fraction which is initially introduced advantageously represents from 2 to 40% by weight, preferably from 4 to 20% by weight, of sodium methoxide with respect to the total amount of sodium methoxide employed.

A 1–30% by weight solution of sodium methoxide in a solvent, such as methanol, is generally introduced.

The amount of sodium methoxide used in implementing the process according to the invention is generally between $1\times10^{-4}$ and $2\times10^{-3}$ mol, preferably $5\times10^{-4}$ and $1\times10^{-3}$ mol, per mole of the heterocyclic alcohol of formula (III).

Mention may in particular be made, as examples of reactants of formula (II), of methyl, ethyl, n-propyl, isopropyl, n-butyl and isobutyl acrylates and methacrylates.

Mention may be made of EIOH, as an example of a heterocyclic alcohol of formula (III).

The reaction of the process according to the invention can be carried out in the presence of an excess of one or other of the reactants. However, it is advisable for the (meth) acrylate of formula (II)/heterocyclic alcohol of formula (III) molar ratio to be between 2 and 5 approximately, preferably between 2.5 and 3.5. By carrying out the reaction with a large molar excess of (meth)acrylate with respect to the heterocyclic alcohol, a solution of compound of formula (I) in the (meth)acrylate is obtained, on conclusion of the reaction, which can be used directly in certain applications, such as the production of paints and coatings or alternatively the treatment of leather.

The reaction of the process according to the invention is preferably carried out in the presence of at least one polymerization inhibitor used, for example, in the proportion of 300 to 1800 ppm, preferably of 600 to 1300 ppm, with respect to the heterocyclic alcohol of formula (III). Mention may in particular be made, as examples of polymerization inhibitors which can be used, of phenothiazine, hydroquinone methyl ether, di-tertbutylcatechol, hydroquinone, p-anilinophenol, paraphenylenediamine and their mixtures in all proportions.

The reaction of the process according to the invention is preferably carried out under a pressure not exceeding atmospheric pressure, for example a pressure of between 0.3 and 1 bar. The reaction is advantageously carried out while bubbling air through, in order to improve the effectiveness of the stabilizers. It is carried out by mixing the (meth) acrylate of formula (II) and the heterocyclic alcohol of formula (III) and by heating the reaction mixture generally to a temperature of between 60° and 90° C. approximately, preferably between 70° and 85° C. approximately, this temperature obviously being dependent on the exact nature of the alcohol and of the (meth)acrylate.

In the implementation of the process according to the invention, it is advisable to wait for maximum dehydration before adding the catalyst, so as to prevent deactivation of the latter by the water. This result can be achieved, for example, by heating the starting mixture of (meth)acrylate of formula (II), of heterocyclic alcohol of formula (III) and of polymerization inhibitors at reflux while separating therefrom, by distillation, the azeotrope of (meth)acrylate and of water when an azeotrope of (meth)acrylate and of water is formed. At this stage, after separation of the distillate, the starting catalyst fraction is introduced into the hot reaction mixture.

The duration of the reaction according to the invention clearly depends on the reaction conditions, such as the temperature, the pressure and the amount of catalyst used, but is generally between 5 and 10 hours approximately. It clearly also depends on the nature of the reactants employed.

The reaction mixture is thus heated at reflux until the head temperature reaches the distillation temperature of the azeotrope of the (meth)acrylate and of the alcohol of formula $R_2OH$ formed by the reaction, when an azeotrope is formed.

The possible excess (meth)acrylate can then be removed by evaporation, so as to isolate the compound of formula (I) from the reaction mixture, generally in the solid state: thus, the acrylate of 1-(2-hydroxyethyl)-imidazolidyl-2-one is a white crystalline solid with a melting temperature of 43° C., which is soluble under cold conditions in ketones, alcohols, aromatic hydrocarbons and water and which is insoluble under cold conditions in saturated hydrocarbons, and which precipitates at 0° C. from ethyl acrylate. The methacrylate of 1-(2-hydroxyethyl)imidazolidyl-2-one is a white crystalline solid with a melting temperature of 47° C. possessing the same solubility properties as the above acrylate. On conclusion of the evaporation operation, the solid crystalline product can additionally be purified by filtration, then washing with petroleum ether, and drying.

The compound (I) can also be isolated by partial evaporation of the (meth)acrylate, then crystallization at a sufficiently low temperature (preferably less than or equal to 0° C.) and for a sufficiently long period of time (which can reach up to 15 hours), then filtration, followed by the purification stages described above.

Finally, a third method for isolating the compound of formula (I) from the solution containing it consists in extracting with water, followed by separating by settling, concentrating the (meth)acrylate and purifying by the stages described above.

The following Examples illustrate the invention without, however, limiting it. In these Examples, the percentages are shown by weight, except when otherwise indicated.

EXAMPLE 1

1458 g of EIOH, 1.823 g of phenothiazine (PTZ) as stabilizer and 3827 g of methyl methacrylate (MMA) are introduced into a 5 litre jacketed glass reactor equipped with a probe for measuring the temperature, a variable speed mechanical stirrer and a packed adiabatic column surmounted by a reflux ratio head. The column head is stabilized with a 0.1% solution of hydroquinone methyl ether (HQME) in MMA.

The contents of the reactor are brought to boiling point, while bubbling air through and under reduced pressure, at a temperature of 75° C. for 1 hour and the water is removed by azeotropic distillation with MMA.

2.12 g of sodium methoxide (MeONa), as a 1% solution in methanol (MeOH), are then introduced into the reactor in a single step. The remainder of the MeONa, as a 1% solution in MeOH, i.e. 40.82 g, is introduced over 7 hours using a metering pump. The pressure is adjusted in order to maintain a temperature of 75° C. in the reactor. The withdrawal of the MMA/MeOH azeotrope is regulated by a column-head set temperature equal to that of the boiling point of the azeotrope at the pressure under consideration, plus 3° C. When the amount of methanol withdrawn corresponds to the expected amount, the reaction is extended by 1 hour, until formation of MeOH is no longer observed (column-head temperature measured at total reflux=boiling temperature of MMA at the pressure under consideration).

After cooling, crude, solid-free EIOM is recovered.

The EIOM yield and the conversion of EIOH are determined from analysis by liquid phase chromatography (HPLC) of the reaction crude, using the following equations:

$$\text{Conversion of } EIOH\ C\ (\%) = \frac{(\text{starting } EIOH - \text{final } EIOH)}{\text{starting } EIOH} \times 100$$

$$EIOM \text{ yield } Y\ (\%) = \frac{\text{Number of moles of } EIOM \text{ formed}}{\text{Number of moles of starting } EIOH} \times 100$$

The results are reported in the Table below, which also includes the data and results of Comparative Example 2.

Comparative Example 2

The same test as in Example 1 is repeated, except that all of the MeONa catalyst is introduced in a single step at the beginning of the synthesis.

TABLE 1

| Example | HPLC analysis of the crude mixture obtained (%) | | | Y (%) | C (%) |
|---|---|---|---|---|---|
| | MMA | EIOH | EIOM | | |
| 1 (of the invention) | 43.58 | 1.44 | 41.66 | 77 | 95.9 |
| 2 (comparartive) | Not analysed: the mixture has two phases, synonymous with a conversion of less than 50% | | | | <50 |

The preceding examples can be repeated with similar success by substituting the generically or specifically described reactants and/or operating conditions of this invention for those used in the preceding examples.

The entire disclosure of all applications, patents and publications, cited above and below, and of corresponding French application 96/11270, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the manufacture of a compound of formula:

$$H_2C=C(R^1)-C(=O)-O-A-N\underset{C(=O)}{\overset{B}{\diagup\diagdown}}NH \quad (I)$$

in which:

$R^1$ represents hydrogen or methyl;

A and B each independently represent a straight or branched hydrocarbon chain having from 2 to 5 carbon atoms, by reaction of at least one (meth)acrylate of formula:

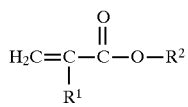

in which:
- $R^1$ has the abovementioned meaning; and
- $R^2$ represents a $C_1$–$C_4$ alkyl group, with a heterocyclic alcohol of formula:

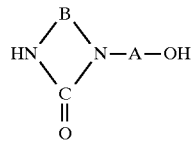

in which A and B have the abovementioned meanings, in the presence of sodium methoxide as catalyst, wherein the sodium methoxide is gradually introduced, as a solution, throughout the synthesis.

2. A process according to claim 1, wherein a portion of the sodium methoxide is introduced at the beginning of the synthesis and the remainder is introduced, continuously or in fractions, throughout the synthesis.

3. A process according to claim 2, wherein 2 to 40% by weight, of sodium methoxide are introduced initially with respect to the total amount of sodium methoxide employed.

4. A process according to claim 3, wherein the percentage of sodium methoxide is 4 to 20% by weight.

5. A process according to claim 1, wherein a 1–30% by weight solution of sodium methoxide in a solvent, is introduced.

6. A process according to claim 5, wherein the solvent is methanol.

7. A process according to claim 1, wherein the sodium methoxide is used in an amount of $1\times10^{-4}$ to $2\times10^{-3}$ mol, per mole of the heterocyclic alcohol of formula (III).

8. A process according to claim 7, wherein the amount of sodium methoxide is $5\times10^{-4}$ to $1\times10^{-3}$ mol.

9. A process according to claim 1, wherein the reaction is carried out at a temperature of between 60° and 90° C.

10. A process according to claim 9, wherein the temperature is between 70° and 85° C.

11. A process according to claim 1, wherein a molar ratio of the (meth)acrylate of formula (II) to the heterocyclic alcohol of formula (III) is used which is between 2 and 5.

12. A process according to claim 11, wherein said molar ratio is between 2.5 and 3.5.

13. A process according to claim 1, wherein the reaction is carried out for a period of time of between 5 and 10 hours.

14. A process according to claim 13, wherein the reaction is conducted at a pressure not exceeding atmospheric pressure.

15. A process according to claim 1, wherein the reaction is carried out in the presence of at least one polymerization inhibitor chosen from phenothiazine, hydroquinone methyl ether, di-tertbutylcatechol, hydroquinone, p-anilinophenol, paraphenylenediamine and their mixtures in all proportions.

16. A process according to claim 15, wherein in the polymerization inhibitor or inhibitors is or are used in a proportion of 300 to 1800.

17. A process according to claim 16, wherein said proportion is 600 to 1300 ppm.

18. A process according to claim 1, wherein the process comprises forming a starting mixture comprising the (meth) acrylate of formula II, the heterocyclic alcohol of formula III and a polymerization inhibitor; heating said starting mixture and subjecting the heated starting mixture to distillation to remove as a distillate an azeotrope of (meth)acrylate and water whereby said water is removed which would otherwise deactivate the catalyst; and adding the catalyst to the resultant distilled starting material throughout the synthesis.

19. In a process for the manufacture of a compound of formula:

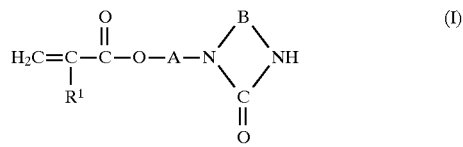

in which:
- $R^1$ represents hydrogen or methyl;
- A and B each independently representsa straight or branched hydrocarbon chain having from 2 to 5 carbon atoms, by reaction of at least one (meth)acrylate of formula:

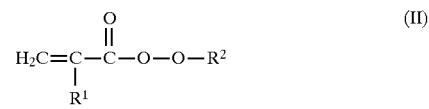

in which:
- $R^1$ has the abovementioned meaning; and
- $R^2$ represents a $C_1$–$C_4$ alkyl group, with a heterocyclic alcohol of formula:

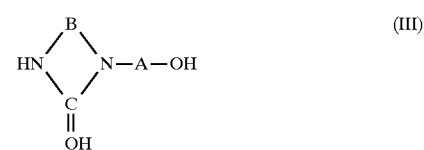

in which A and B have the abovementioned meanings, in the presence of sodium methoxide as catalyst, the improvement comprising adding said sodium methoxide as a solution sufficiently gradually as a solution throughout the synthesis so as to diminish Michael addition side reactions and result in a substantially higher yield of compound I as compared to the introduction of all the catalyst at the beginning of the reaction.

* * * * *